(12) United States Patent
Toledano et al.

(10) Patent No.: US 12,357,602 B2
(45) Date of Patent: Jul. 15, 2025

(54) COMPOSITIONS COMPRISING ENCAPSULATED TRETINOIN

(71) Applicant: SOL-GEL TECHNOLOGIES LTD., Ness Ziona (IL)

(72) Inventors: Ofer Toledano, Kfar Saba (IL); Karine Neimann, Ness Ziona (IL); Maya Erlich, Ness Ziona (IL); Dorit Marco, Rehovot (IL)

(73) Assignee: Mayne Pharma LLC, Raleigh, NC (US)

( * ) Notice: Subject to any disclaimer, the term of this patent is extended or adjusted under 35 U.S.C. 154(b) by 0 days.

(21) Appl. No.: 16/033,260

(22) Filed: Jul. 12, 2018

(65) Prior Publication Data

US 2019/0015366 A1    Jan. 17, 2019

Related U.S. Application Data

(60) Provisional application No. 62/531,402, filed on Jul. 12, 2017.

(51) Int. Cl.
| | |
|---|---|
| *A61K 31/202* | (2006.01) |
| *A61K 9/00* | (2006.01) |
| *A61K 9/06* | (2006.01) |
| *A61K 9/107* | (2006.01) |
| *A61K 9/50* | (2006.01) |
| *A61K 31/203* | (2006.01) |

(52) U.S. Cl.
CPC .......... *A61K 31/202* (2013.01); *A61K 9/0014* (2013.01); *A61K 9/06* (2013.01); *A61K 9/107* (2013.01); *A61K 9/501* (2013.01); *A61K 31/203* (2013.01)

(58) Field of Classification Search
CPC .. A61K 31/203; A61K 31/327; A61K 31/202; A61K 9/0014; A61K 9/06; A61K 9/107; A61K 9/501; A61K 2300/00
USPC ........................................................ 424/490
See application file for complete search history.

(56) References Cited

U.S. PATENT DOCUMENTS

| | | |
|---|---|---|
| 1,387,107 A | 8/1921 | Carr |
| 1,671,956 A | 5/1928 | Sime |
| 2,885,366 A | 5/1959 | Iler |
| 3,785,798 A | 1/1974 | Horai et al. |
| 3,826,670 A | 7/1974 | Rees |

(Continued)

FOREIGN PATENT DOCUMENTS

| | | |
|---|---|---|
| AU | 764016 B1 | 8/2003 |
| AU | 2008246274 A1 | 12/2008 |

(Continued)

OTHER PUBLICATIONS

Aizawa et al. "Preparation of Spherical Hydrous Silica Oxide Particles under Acidic Condition via Sol-Gel Processing" Journal of Sol-Gel Science and Technology. Dec. 1, 2000;19(1-3):329-32.

(Continued)

*Primary Examiner* — Isaac Shomer
*Assistant Examiner* — Bryan James Rego
(74) *Attorney, Agent, or Firm* — Mark S. Cohen; PEARL COHEN ZEDEK LATZER BARATZ LLP (57) ABSTRACT

The present application is directed to compositions comprising microcapsules comprising encapsulated tretinoin, wherein the microcapsule size is less than 50 μm; and to methods of use thereof.

14 Claims, 1 Drawing Sheet

(56) References Cited

U.S. PATENT DOCUMENTS

| | | |
|---|---|---|
| 3,906,108 A | 9/1975 | Felty |
| 3,957,971 A | 5/1976 | Oleniacz |
| 4,129,645 A | 12/1978 | Barnett et al. |
| 4,169,069 A | 9/1979 | Unger et al. |
| 4,349,456 A | 9/1982 | Sowman |
| 4,350,681 A | 9/1982 | Fulton, Jr. |
| 4,361,584 A | 11/1982 | Fulton, Jr. |
| 4,387,107 A | 6/1983 | Klein et al. |
| 4,444,746 A | 4/1984 | Harvey et al. |
| 4,464,317 A | 8/1984 | Thies et al. |
| 4,497,794 A | 2/1985 | Klein et al. |
| 4,606,913 A | 8/1986 | Aronson et al. |
| 4,671,956 A | 6/1987 | Bouillon et al. |
| 4,686,211 A | 8/1987 | Hara et al. |
| 4,690,825 A | 9/1987 | Won |
| 4,692,329 A | 9/1987 | Klein et al. |
| 4,769,080 A | 9/1988 | Clark et al. |
| 4,880,851 A | 11/1989 | Yamamoto |
| 4,891,211 A | 1/1990 | Winston |
| 4,931,362 A | 6/1990 | Zsifkovits et al. |
| 4,960,772 A | 10/1990 | Sebag et al. |
| 4,988,744 A | 1/1991 | Yamamoto |
| 5,086,075 A | 2/1992 | De Villez |
| 5,126,915 A | 6/1992 | Pepin et al. |
| 5,145,675 A | 9/1992 | Won |
| 5,165,914 A | 11/1992 | Vlock |
| 5,185,155 A | 2/1993 | Behan et al. |
| 5,200,334 A | 4/1993 | Dunn et al. |
| 5,223,250 A | 6/1993 | Mitchell et al. |
| 5,269,840 A | 12/1993 | Morris et al. |
| 5,292,801 A | 3/1994 | Avnir et al. |
| 5,310,721 A | 5/1994 | Lo |
| 5,318,797 A | 6/1994 | Matijevic et al. |
| 5,387,622 A | 2/1995 | Yamamoto |
| 5,401,517 A | 3/1995 | Meyers et al. |
| 5,446,028 A | 8/1995 | Klein et al. |
| 5,455,048 A | 10/1995 | Lahmani et al. |
| 5,466,446 A | 11/1995 | Stiefel et al. |
| 5,468,471 A | 11/1995 | Zecchino et al. |
| 5,472,491 A | 12/1995 | Duschek et al. |
| 5,500,223 A | 3/1996 | Behan et al. |
| 5,520,917 A | 5/1996 | Mizuguchi et al. |
| 5,556,617 A | 9/1996 | Ribier et al. |
| 5,587,170 A | 12/1996 | Casey et al. |
| 5,591,453 A | 1/1997 | Ducheyne et al. |
| 5,607,664 A | 3/1997 | Ascione et al. |
| 5,632,996 A | 5/1997 | Ramirez |
| 5,635,609 A | 6/1997 | Levy et al. |
| 5,635,809 A | 6/1997 | Ganser et al. |
| 5,650,311 A | 7/1997 | Avnir et al. |
| 5,670,209 A | 9/1997 | Wyckoff |
| 5,672,301 A | 9/1997 | Orly et al. |
| 5,690,923 A | 11/1997 | DeVringer et al. |
| 5,691,060 A | 11/1997 | Levy |
| 5,700,451 A | 12/1997 | Yue et al. |
| 5,720,949 A | 2/1998 | Davis |
| 5,733,531 A | 3/1998 | Mitchnick et al. |
| 5,739,020 A | 4/1998 | Pope |
| 5,767,098 A | 6/1998 | Klein et al. |
| 5,785,977 A | 7/1998 | Breithbarth |
| 5,792,250 A | 8/1998 | Braun et al. |
| 5,851,538 A | 12/1998 | Froix et al. |
| 5,874,105 A | 2/1999 | Watkins et al. |
| 5,876,699 A | 3/1999 | Disomma et al. |
| 5,879,716 A | 3/1999 | Katz et al. |
| 5,891,476 A | 4/1999 | Reo et al. |
| 5,895,757 A | 4/1999 | Pope et al. |
| 5,906,811 A | 5/1999 | Hersh |
| 5,912,016 A | 6/1999 | Perrier et al. |
| 5,914,101 A | 6/1999 | Tapley et al. |
| 5,914,104 A | 6/1999 | Moore, Jr. |
| 5,914,116 A | 6/1999 | Suares et al. |
| 5,932,228 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko et al. |
| 6,077,522 A | 6/2000 | Scher et al. |
| 6,090,399 A | 8/2000 | Bershad |
| 6,096,765 A | 8/2000 | Bershad |
| 6,103,267 A | 8/2000 | Mitchnik et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,159,453 A | 12/2000 | Avnir et al. |
| 6,171,600 B1 | 1/2001 | Dahms |
| 6,197,757 B1 | 3/2001 | Perrier et al. |
| 6,200,375 B1 | 3/2001 | Guez et al. |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,270,836 B1 | 8/2001 | Holman |
| 6,280,746 B1 | 8/2001 | Arquette et al. |
| 6,303,149 B1 | 10/2001 | Magdassi et al. |
| 6,303,290 B1 | 10/2001 | Liu et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,479,146 B1 | 11/2002 | Caruso et al. |
| 6,495,352 B1 | 12/2002 | Brinker et al. |
| 6,534,044 B1 | 3/2003 | Wada et al. |
| 6,537,583 B1 | 3/2003 | Dupuis et al. |
| 6,607,713 B1 | 8/2003 | Chodorowski et al. |
| 6,616,947 B1 | 9/2003 | Depuis et al. |
| 6,646,947 B2 | 11/2003 | Fukui et al. |
| 6,703,032 B2 | 3/2004 | Gers-barlag |
| 6,855,335 B2 | 2/2005 | Seok et al. |
| 6,875,264 B2 | 4/2005 | Zimmermann et al. |
| 6,913,825 B2 | 7/2005 | Ostafin et al. |
| 6,939,552 B2 | 9/2005 | Ansara et al. |
| 6,979,440 B2 | 12/2005 | Shefer et al. |
| 7,001,592 B1 | 2/2006 | Traynor et al. |
| 7,037,513 B1 | 5/2006 | Traynor et al. |
| 7,202,991 B2 | 4/2007 | Zhang et al. |
| 7,758,888 B2 | 7/2010 | Lapidot et al. |
| 8,039,020 B2 | 10/2011 | Lapidot et al. |
| 8,158,109 B2 | 4/2012 | Abram et al. |
| 8,568,704 B2 | 10/2013 | Mallard et al. |
| 9,687,465 B2 | 6/2017 | Sertchook et al. |
| 9,868,103 B2 * | 1/2018 | Toledano ............ A61P 17/04 |
| 10,420,743 B2 | 9/2019 | Toledano et al. |
| 10,514,828 B2 | 12/2019 | Pope et al. |
| 10,525,433 B2 | 1/2020 | Toledano et al. |
| 10,653,899 B2 | 5/2020 | Toledano et al. |
| 12,053,546 B2 * | 8/2024 | Toledano ............ A61K 9/06 |
| 2002/0064541 A1 | 5/2002 | Lapidot et al. |
| 2002/0144192 A1 | 10/2002 | Owari |
| 2002/0151527 A1 | 10/2002 | Wiegand et al. |
| 2002/0193321 A1 | 12/2002 | Vishnupad et al. |
| 2003/0004118 A1 | 1/2003 | Vishnupad et al. |
| 2003/0157330 A1 | 8/2003 | Ostafin et al. |
| 2003/0170196 A1 | 9/2003 | Orsoni et al. |
| 2004/0096419 A1 | 5/2004 | Golz-Berner et al. |
| 2004/0101566 A1 | 5/2004 | Cooper et al. |
| 2004/0157766 A1 | 8/2004 | Embil et al. |
| 2004/0202682 A1 | 10/2004 | Emrick et al. |
| 2004/0202726 A1 | 10/2004 | DeShay |
| 2004/0234738 A1 | 11/2004 | Jahns et al. |
| 2005/0037087 A1 | 2/2005 | Lapidot et al. |
| 2005/0045181 A1 | 3/2005 | Philipps et al. |
| 2005/0133036 A1 | 6/2005 | Steindorf |
| 2005/0156340 A1 | 7/2005 | Valianatos et al. |
| 2005/0201955 A1 | 9/2005 | Bunger et al. |
| 2005/0208134 A1 | 9/2005 | Magdassi et al. |
| 2005/0276807 A1 | 12/2005 | Skurkovich et al. |
| 2006/0008440 A1 | 1/2006 | Blatt et al. |
| 2006/0014834 A1 | 1/2006 | Vishnupad et al. |
| 2006/0128808 A1 | 6/2006 | Arsonnaud et al. |
| 2006/0167138 A1 | 7/2006 | Ishii et al. |
| 2006/0199011 A1 | 9/2006 | Jahns |

(56) References Cited

U.S. PATENT DOCUMENTS

| | | |
|---|---|---|
| 2006/0204530 A1 | 9/2006 | Ramirez et al. |
| 2006/0251687 A1 | 11/2006 | Lapidot et al. |
| 2006/0292093 A1 | 12/2006 | Carola et al. |
| 2007/0003585 A1 | 1/2007 | Clark et al. |
| 2007/0207113 A1 | 9/2007 | Joerger et al. |
| 2007/0292626 A1 | 12/2007 | Traynor et al. |
| 2007/0292676 A1 | 12/2007 | Naigertsik et al. |
| 2008/0064761 A1 | 3/2008 | Gondek et al. |
| 2008/0249192 A1 | 10/2008 | Goget et al. |
| 2008/0292560 A1 | 11/2008 | Tamarkin et al. |
| 2009/0041922 A1 | 2/2009 | Kuhnle et al. |
| 2009/0081262 A1* | 3/2009 | Toledano ............... A61K 8/11 424/490 |
| 2009/0226380 A1 | 9/2009 | Clark et al. |
| 2009/0270259 A1 | 10/2009 | Auweter et al. |
| 2009/0304820 A1 | 12/2009 | Modi |
| 2010/0016443 A1* | 1/2010 | Toledano ............... A01N 25/26 514/699 |
| 2010/0029765 A1 | 2/2010 | Gupta et al. |
| 2010/0047357 A1 | 2/2010 | Toledano et al. |
| 2010/0143285 A1 | 6/2010 | Mallard et al. |
| 2010/0255107 A1 | 10/2010 | Lapidot et al. |
| 2011/0045037 A1 | 2/2011 | Tamarkin et al. |
| 2011/0052515 A1 | 3/2011 | Kaoukhov |
| 2011/0177951 A1* | 7/2011 | Toledano ............... A01N 25/28 504/342 |
| 2011/0237555 A1 | 9/2011 | Sanchez et al. |
| 2012/0015014 A1 | 1/2012 | Lapidot et al. |
| 2012/0064135 A1 | 3/2012 | Levin et al. |
| 2012/0202695 A1* | 8/2012 | Toledano ............. A61K 9/5115 424/490 |
| 2012/0269874 A1 | 10/2012 | Toledano et al. |
| 2013/0095185 A1 | 4/2013 | Toledano et al. |
| 2014/0147396 A1* | 5/2014 | Sertchook ............ A61K 9/1075 424/59 |
| 2015/0190372 A1 | 7/2015 | Djedour |
| 2017/0281571 A1 | 10/2017 | Sertchook et al. |
| 2018/0117369 A1 | 5/2018 | Toledano et al. |
| 2018/0207451 A1 | 7/2018 | Toledano et al. |
| 2019/0015368 A1 | 1/2019 | Arkin et al. |
| 2019/0015369 A1 | 1/2019 | Arkin et al. |
| 2019/0336464 A1 | 7/2019 | Toledano et al. |

FOREIGN PATENT DOCUMENTS

| | | |
|---|---|---|
| AU | 2002364437 B2 | 5/2011 |
| DE | 4416003 | 11/1995 |
| DE | 19811900 A1 | 9/1999 |
| DE | 202011100767 U1 | 12/2011 |
| EP | 0972563 A1 | 1/2000 |
| EP | 1511802 B1 | 9/2010 |
| GB | 1399344 A | 7/1975 |
| GB | 2088717 A | 6/1982 |
| GB | 2416524 A | 2/2006 |
| JP | H0240302 | 2/1990 |
| JP | H02251240 A | 10/1990 |
| JP | H03229634 A | 10/1991 |
| JP | H03243663 A | 10/1991 |
| JP | H07173452 A | 7/1995 |
| JP | H9110463 A | 4/1997 |
| JP | 09-235217 A | 9/1997 |
| JP | 02292824 A | 10/2002 |
| JP | H01113436 A | 5/2009 |
| RU | 2314093 | 1/2008 |
| WO | WO 1997/007676 A1 | 3/1997 |
| WO | WO 1997/032561 A1 | 9/1997 |
| WO | WO 1997/040106 A1 | 10/1997 |
| WO | WO 1997/045367 A1 | 12/1997 |
| WO | WO 1998/015183 A1 | 4/1998 |
| WO | WO 1998/031333 A1 | 7/1998 |
| WO | WO 1999/003450 | 1/1999 |
| WO | WO 1999/047253 A1 | 9/1999 |
| WO | WO 2000/009652 A2 | 2/2000 |
| WO | WO 2000/025781 | 5/2000 |
| WO | WO 2000/047236 A1 | 8/2000 |
| WO | WO 2000/071084 A1 | 11/2000 |
| WO | WO 2000/072806 A2 | 12/2000 |
| WO | WO 2001/012221 A1 | 2/2001 |
| WO | WO 2001/013924 A1 | 3/2001 |
| WO | WO 2001/051196 A1 | 7/2001 |
| WO | WO 2001/058451 A1 | 8/2001 |
| WO | WO 2001/080823 A2 | 11/2001 |
| WO | WO 2002/085113 A1 | 10/2002 |
| WO | WO 2003/003497 A1 | 1/2003 |
| WO | WO 2003/034979 A2 | 5/2003 |
| WO | WO 2003/039510 A1 | 5/2003 |
| WO | WO 2003/066209 A1 | 8/2003 |
| WO | WO 2003/086419 | 10/2003 |
| WO | WO 2003/099295 A1 | 12/2003 |
| WO | WO 2003/104319 A1 | 12/2003 |
| WO | WO 2004/064769 A2 | 8/2004 |
| WO | WO 2004/064803 A1 | 8/2004 |
| WO | WO 2004/069135 A2 | 8/2004 |
| WO | WO 2004/069216 A1 | 8/2004 |
| WO | WO 2004/081222 A2 | 9/2004 |
| WO | WO 2005/009604 A1 | 2/2005 |
| WO | WO 2007/000316 A1 | 1/2007 |
| WO | WO 2007/015243 A2 | 2/2007 |
| WO | WO 2007/036939 A2 | 4/2007 |
| WO | WO-2007092312 A2 | 8/2007 |
| WO | WO 2008/002637 A2 | 1/2008 |
| WO | WO 2008/030749 A2 | 3/2008 |
| WO | WO 2008/057411 | 5/2008 |
| WO | WO 2008/072239 A2 | 6/2008 |
| WO | WO 2008/083092 A2 | 7/2008 |
| WO | WO 2008/093346 A2 | 7/2008 |
| WO | WO 2008/093347 A2 | 8/2008 |
| WO | WO 2006/127172 A2 | 11/2008 |
| WO | WO 2008/133482 A1 | 11/2008 |
| WO | WO 2008/134908 A1 | 11/2008 |
| WO | WO-2009051839 A1 | 4/2009 |
| WO | WO 2009/148584 A1 | 12/2009 |
| WO | WO 2010/013250 A1 | 2/2010 |
| WO | WO 2011/049547 A1 | 4/2011 |
| WO | WO 2011/080741 A2 | 7/2011 |
| WO | WO 2012/037000 A1 | 3/2012 |
| WO | WO-2013001536 A1 | 1/2013 |
| WO | WO-2019012536 A1 | 1/2019 |

OTHER PUBLICATIONS

Alava et al. "Temperature-responsive emulsions: The effect of added surfactant" Colloids and Surfaces A: Physicochemical and Engineering Aspects. Dec. 1, 2005;270:18-25.

"Aliphatic Compound" obtained online via www.wikipedia.com (2018).

Aveyard et al. "Emulsions stabilised solely by colloidal particles" Advances in Colloid and Interface Science. Feb. 28, 2003;100:503-46.

Bashir and Maibach, The Chemistry and Manufacture of Cosmetics V1 Chapter 5 third ed. pp. 163-182 (2000).

Beelen et al. "The role of aging on the formation of porous silica" Preparation of Catalysts VI. Jan. 1, 1995:33-48.

Benzoyl Peroxide ("BPO", Chem and Tech. Assess. 2004, 61st JECFA, 1-6, http://www.fao.org/fileadmin/templates/ gns/pdf/jecfa/cta/63/Benzoylperoxide.pdf).

Binks et al. "Effects of pH and salt concentration on oil-in-water emulsions stabilized solely by nanocomposite microgel particles" Langmuir. Feb. 28, 2006;22(5):2050-7.

Binks et al. "Inversion of silica-stabilized emulsions induced by particle concentration" Langmuir. Apr. 12, 2005;21(8):3296-302.

Binks et al. Nanoparticle silica-stabilised oil-in-water emulsions: improving emulsion stability. Colloids and Surfaces A: Physicochemical and Engineering Aspects. Feb. 1, 2005;253(1-3):105-15.

Binks et al. "Naturally occurring spore particles at planar fluid interfaces and in emulsions" Langmuir. Aug. 30, 2005;21(18):8161-7.

Binks BP. "Particles as surfactants—similarities and differences" Current opinion in colloid & interface science. Mar. 1, 2002;7(1-2):21-41.

(56) References Cited

OTHER PUBLICATIONS

Binks et al. "Solid wettability from surface energy components: relevance to Pickering emulsions" Langmuir. Feb. 19, 2002;18(4):1270-3.
Bon et al. "Pickering stabilization as a tool in the fabrication of complex nanopatterned silica microcapsules" Langmuir. Sep. 11, 2007;23(19):9527-30.
Bonnet et al. "Stabilization of caseinate-covered oil droplets during acidification with high methoxyl pectin" Journal of agricultural and food chemistry. Nov. 2, 2005;53(22):8600-6.
Breneman et al. "Double-blind, randomized, vehicle-controlled clinical trial of once-daily benzoyl peroxide/clindamycin topical gel in the treatment of patients with moderate to severe rosacea" International journal of dermatology. May 2004;43(5):381-7.
Brinker et al. "Sol-Gel Science. The Physics and Chemistry of Sol-Gel Processing" Academic Press, Inc., San Diego, CA, pp. 104-105, 134-137, 146-147, and 150-151. (1990).
Brinker et al., "The Physics and Chemistry of Sol-Gel Processing", Sol-Gel Science, pp. 562-563, May 1990.
Bugnon P. "Surface treatment of pigments. Treatment with inorganic materials" Progress in organic coatings. Sep. 1, 1996;29(1-4):39-43.
Bugosh J. "Colloidal alumina—the chemistry and morphology of colloidal boehmite" The Journal of Physical Chemistry. Oct. 1961;65(10):1789-93.
Burkle GmbH, "Viscosity of Liquids", 2011.
Butler et al. "An emulsion method for producing fine, low density, high surface area silica powder from alkoxides" Journal of materials science. Jan. 1, 1996;31(7):1675-80.
Chung et al. "Aqueous Synthesis of Y2O2S: Eu/Silica Core-Shell Particles" Journal of the American Ceramic Society. May 2005;88(5):1341-4.
Clegg et al. "Colloid-stabilized emulsions: behaviour as the interfacial tension is reduced" Journal of Physics: Condensed Matter. Oct. 28, 2005;17(45):S3433.
Colver et al. "Cellular polymer monoliths made via pickering high internal phase emulsions" Chemistry of materials. Apr. 3, 2007;19(7):1537-9.
Compilation under Creative Commons Attribution-Share Alike 3.0, "Viscosity", undated, pp. 1-20.
Culp et al. "Rosacea: a review" P & T: a peer-reviewed journal for formulary management. Jan. 2009;34(1):38.
Dai et al. "Self-assembled structure of nanoparticles at a liquid-liquid interface" Langmuir. Mar. 29, 2005;21(7):2641-3.
Danov et al. "Electric forces induced by a charged colloid particle attached to the water-nonpolar fluid interface" Journal of colloid and interface science. Jun. 1, 2006;298(1):213-31.
Del Rosso et al. "Consensus recommendations from the American Acne & Rosacea Society on the management of rosacea, part 2: a status report on topical agents" Cutis. Dec. 2013;92(6):277-84.
Del Rosso et al. "Absence of degradation of tretinoin when benzoyl peroxide is combined with an optimized formulation of tretinoin gel (0.05%)" The Journal of clinical and aesthetic dermatology. Oct. 2010;3(10):26.
Dickson et al. "Interactions of Core-Shell Silica Nanoparticles in Liquid Carbon Dioxide Measured by Dynamic Light Scattering" Industrial & engineering chemistry research. Aug. 2, 2006;45(16):5603-13.
Ding et al. "Influence of particle hydrophobicity on particle-assisted wetting" Langmuir. Feb. 15, 2005;21(4):1371-6.
Dorobantu et al. "Stabilization of oil-water emulsions by hydrophobic bacteria" Appl. Environ. Microbiol.. Oct. 1, 2004;70(10):6333-6.
Dun et al. "Layer-by-layer self-assembly of multilayer zirconia nanoparticles on silica spheres for HPLC packings" Analytical chemistry. Sep. 1, 2004;76(17):5016-23.
"Environmental Protection Agency", Federal Register, 2002, vol. 67, No. 94 and 40 CFR part 180, pp. 34616-34620.
Fain et al. "Surface Activity of Solid Emulsifiers" Industrial & Engineering Chemistry. Jan. 1939;31(1):48-51.

Fernandez et al. "New green surfactants for emulsion polymerization" Progress in organic coatings. Aug. 1, 2005;53(4):246-55.
Fireman et al. "A look at emerging delivery systems for topical drug products" Dermatologic therapy. Sep. 2011;24(5):477-88.
Flux, "Viscosity Chart", undated, p. 21.
Fujii et al. "Hydroxyapatite nanoparticles as stimulus-responsive particulate emulsifiers and building block for porous materials" Journal of colloid and interface science. Nov. 1, 2007;315(1):287-96.
Futamura et al. "A systematic review of Investigator Global Assessment (IGA) in atopic dermatitis (AD) trials: many options, no standards" Journal of the American Academy of Dermatology. Feb. 1, 2016;74(2):288-94.
Giermanska-Kahn et al. "A new method to prepare monodisperse Pickering emulsions" Langmuir. Apr. 2, 2002;18(7):2515-8.
Goldgar et al. "Treatment options for acne rosacea" American family physician. Sep. 1, 2009;80(5) 461-8.
Gonzenbach et al. "Stabilization of foams with inorganic colloidal particles" Langmuir. Dec. 19, 2006;22(26):10983-8.
Gonzenbach et al. "Ultrastable particle-stabilized foams" Angewandte Chemie International Edition. May 19, 2006;45(21):3526-30.
Graber, Emmy "Treatment of Acne Vulgaris" UpToDate.com, Jul. 2016.
Guttula et al. "Self-assembly of colloidal lattices at pickering emulsion interfaces." PhD diss., 2007.
Hall et al. "Cocondensation of organosilica hybrid shells on nanoparticle templates: a direct synthetic route to functionalized core-shell colloids" Langmuir. Feb. 8, 2000;16(3):1454-6.
Hannisdal et al. "Particle-stabilized emulsions: effect of heavy crude oil components pre-adsorbed onto stabilizing solids" Colloids and Surfaces A: Physicochemical and Engineering Aspects. Mar. 15, 2006;276(1-3):45-58.
Haq et al. "Preparation and properties of uniform coated inorganic colloidal particles 9. Titania on copper compounds" Colloids and Surfaces A: Physicochemical and Engineering Aspects. Dec. 13, 1993;81:153-9.
Hardikar et al. "Coating of nanosize silver particles with silica" Journal of Colloid and Interface Science. Jan. 1, 2000;221(1):133-6.
Havre et al. "Emulsion stabilization by means of combined surfactant multilayer (D-phase) and asphaltene particles" Colloids and Surfaces A: Physicochemical and Engineering Aspects. Nov. 1, 2003;228(1-3):131-42.
He et al. "Novel Janus Cu2 (OH) 2CO3/CuS microspheres prepared via a Pickering emulsion route" Journal of colloid and interface science. Feb. 15, 2007;306(2):296-9.
He et al. "Preparation of porous and nonporous silica nanofilms from aqueous sodium silicate" Chemistry of materials. Aug. 26, 2003;15(17):3308-13.
Helseth et al. "Colloidal rings in a liquid mixture" Langmuir. Aug. 2, 2005;21(16):7271-5.
Hench et al. "The sol-gel process" Chemical reviews. Jan. 1, 1990;90(1):33-72.
Horozov et al. "Effect of particle hydrophobicity on the formation and collapse of fumed silica particle monolayers at the oil-water interface" Colloids and Surfaces A: Physicochemical and Engineering Aspects. Jul. 20, 2006;282:377-86.
Horozov et al. "Structure and stability of silica particle monolayers at horizontal and vertical octane-water interfaces" Langmuir. Aug. 2, 2005;21(16):7405-12.
Horozov et al. "Particle-stabilized emulsions: a bilayer or a bridging monolayer?" Angewandte Chemie. Jan. 23, 2006;118(5):787-90.
Hsu et al. "Paper whiteners: I. Titania coated silica" Journal of Colloid and Interface Science. Mar. 1, 1993;156(1):56-65.
Ikeda et al. "Direct Observation of Amphiphilic Silica Particles Assembled at an Oil-Water Interface" Chemistry letters. Sep. 10, 2005;34(10):1386-7.
Iler, Ralph K. "The Chemistry of Silica, Solubility, Polymerization, Colloid and Surface Properties, and Biochemistry" John Wiley & Sons, pp. 366-367 (1979).
Iler R. "Silica Gels" The Chemistry of Silica. 1979:510-33.
International Search Report for PCT Application No. PCT/IL2018/050765 dated Sep. 20, 2018.

(56) References Cited

OTHER PUBLICATIONS

Iskandar et al. "Control of the morphology of nanostructured particles prepared by the spray drying of a nanoparticle sol" Journal of Colloid and Interface Science. Sep. 15, 2003;265(2):296-303.
Iskandar et al. "Preparation of microencapsulated powders by an aerosol spray method and their optical properties" Advanced Powder Technology. Jan. 1, 2003;14(3):349-68.
Jean et al. "Y2O2S: Eu red phosphor powders coated with silica" Journal of the American Ceramic Society. Aug. 2000;83(8):1928-34.
Jenning et al. "Comparison of wax and glyceride solid lipid nanoparticles (SLN®)" International journal of pharmaceutics. Mar. 10, 2000;196(2):219-22.
Jenning et al. "Encapsulation of retinoids in solid lipid nanoparticles (SLN)" Journal of microencapsulation. Jan. 1, 2001;18(2):149-58.
Jesionowski T. "Characterization of silicas precipitated from solution of sodium metasilicate and hydrochloric acid in emulsion medium" Powder technology. Sep. 3, 2002;127(1):56-65.
Kaptay G. "On the equation of the maximum capillary pressure induced by solid particles to stabilize emulsions and foams and on the emulsion stability diagrams" Colloids and Surfaces A: Physicochemical and Engineering Aspects. Jul. 20, 2006;282:387-401.
Khrenov et al. "The formation of hydrophobic inorganic nanoparticles in the presence of amphiphilic copolymers" Colloid and Polymer Science. May 1, 2006;284(8):927-34.
Kim et al. "Monodisperse hollow titania nanospheres prepared using a cationic colloidal template" Journal of colloid and interface science. Dec. 15, 2006;304(2):370-7.
Kim et al. "Effect of aqueous phase composition on the stability of a silica-stabilized water-in-oil emulsion" Journal of the Society of Cosmetic Scientists of Korea. 2004;30(3):353-9.
Kortesuo et al. "Effect of synthesis parameters of the sol-gel-processed spray-dried silica gel microparticles on the release rate of dexmedetomidine" Biomaterials. Jul. 1, 2002;23(13):2795-801.
Kortesuo et al. "In vitro evaluation of sol-gel processed spray dried silica gel microspheres as carrier in controlled drug delivery" International journal of pharmaceutics. May 10, 2000;200(2):223-9.
Korting et al. "Current topical and systemic approaches to treatment of rosacea" Journal of the European Academy of Dermatology and Venereology. Aug. 1, 2009;23(8):876-82.
Kralchevsky et al. "On the thermodynamics of particle-stabilized emulsions: curvature effects and catastrophic phase inversion" Langmuir. Jan. 4, 2005;21(1):50-63.
Kruglyakov et al. "Investigation of the influence of capillary pressure on stability of a thin layer emulsion stabilized by solid particles" Colloids and Surfaces A: Physicochemical and Engineering Aspects. Aug. 1, 2005;263(1-3):330-5.
Lan et al. "Synthesis of bilayer oleic acid-coated Fe3O4 nanoparticles and their application in pH-responsive Pickering emulsions" Journal of colloid and interface science. Jun. 1, 2007;310(1):260-9.
Lapidot et al. "Advanced sunscreens: UV absorbers encapsulated in sol-gel glass microcapsules" Journal of sol-gel science and technology. Jan. 1, 2003;26(1-3):67-72.
Le et al. "Theoretical and experimental studies on the silica hollow spheres" Journal of non-crystalline solids. Feb. 1, 2007;353(2):164-9.
Leunissen et al. "Electrostatics at the oil-water interface, stability, and order in emulsions and colloids" Proceedings of the National Academy of Sciences. Feb. 20, 2007;104(8):2585-90.
Leyden et al. "Comparison of the efficacy and safety of a combination topical gel formulation of benzoyl peroxide and clindamycin with benzoyl peroxide, clindamycin and vehicle gel in the treatments of acne vulgaris" American journal of clinical dermatology. Feb. 1, 2001;2(1):33-9.
Li et al. "Fabrication of porous hollow silica nanoparticles and their applications in drug release control" Journal of Controlled Release. Aug. 11, 2004;98(2):245-54.
Liu et al. "Polymer microspheres stabilized by titania nanoparticles" Materials letters. Dec. 1, 2006;60(29-30):3731-4.
Liz-Marzán et al. "Synthesis of nanosized gold-silica core-shell particles" Langmuir. Sep. 4, 1996;12(18):4329-35.
"Ludox TM-50 colloidal silica", Sigma-Aldrich, website: http://www.sigmaaldrich.com/catalog/producl/aldrich/420778?lang=en&region=US, downloaded Aug. 29, 2012.
Maibach, Howard "Reduction of Skin Irritancy with MicrospongeÂ® Topical Delivery." (2008): 45-7.
Makarova et al. "Adsorption and encapsulation of fluorescent probes in nanoparticles" The Journal of Physical Chemistry B. Oct. 28, 1999;103(43):9080-4.
Manoharan VN. "Colloidal spheres confined by liquid droplets: Geometry, physics, and physical chemistry" Solid state communications. Sep. 1, 2006;139(11-12):557-61.
"Martindale: The extra Pharmacopeia," Pharmaceutical Press, pp. 1093-1095, 1999.
Melle et al. "Pickering emulsions with controllable stability" Langmuir. Mar. 15, 2005;21(6):2158-62.
Menner et al. "Particle-stabilized surfactant-free medium internal phase emulsions as templates for porous nanocomposite materials: poly-pickering-foams". Langmuir. Feb. 27, 2007;23(5):2398-403.
Merikhi et al. "Adhesion of colloidal SiO2 particles on ZnS-type phosphor surfaces" Journal of colloid and interface science. Aug. 1, 2000;228(1):121-6.
Midmore BR. "Preparation of a novel silica-stabilized oil/water emulsion" Colloids and Surfaces A: Physicochemical and Engineering Aspects. Jan. 30, 1998;132(2-3):257-65.
Mikrajuddin et al. "Stable photoluminescence of zinc oxide quantum dots in silica nanoparticles matrix prepared by the combined sol-gel and spray drying method" Journal of Applied Physics. Jun. 1, 2001;89(11):6431-4.
Miller et al. "Composite interfacial layers containing micro-size and nano-size particles" Advances in Colloid and Interface Science. Dec. 21, 2006;128:17-26.
Montes et al. "Topical treatment of acne rosacea with benzoyl peroxide acetone gel" Cutis. Aug. 1983;32(2):185-90.
Nakatsuka T. "Surface modification of inorganic pigments with organic UV absorbers" Colloids and surfaces. Jan. 1, 1988;34(4):323-34.
National Rosacea Society "All about Rosacea" downloaded Apr. 23, 2018 from: https://www.rosacea.org/patients/allaboutrosacea.php.
National Rosacea Society "New Study Examines Differences Between Rosacea and Acne" downloaded Apr. 23, 2018 from: https://www.rosacea.org/weblog/new-study-examines-differences-between-rosacea-and-acne.
National Rosacea Society 'Quick Links' downloaded Jun. 19, 2018 from: https://www.rosacea.org/.
Neirynck et al. "Influence of pH and biopolymer ratio on sodium caseinate-guar gum interactions in aqueous solutions and in O/W emulsions" Food hydrocolloids. Jul. 1, 2007;21(5-6):862-9.
Ngai et al. "Novel emulsions stabilized by pH and temperature sensitive microgels" Chemical communications. 2005(3):331-3.
Ni et al. "Poly (dimethylamino) ethyl methacrylate for use as a surfactant in the miniemulsion polymerization of styrene" Langmuir. Jul. 4, 2006;22(14):6016-23.
Nokhodchi et al. "The effect of formulation type on the release of benzoyl peroxide from microsponges" Iranian Journal of Pharmaceutical Sciences. Mar. 1, 2005;1(3):131-42.
Oh et al. "Synthesis of silica microspheroids for templates in W/O reverse emulsion" Colloids and Surfaces A: Physicochemical and Engineering Aspects. Nov. 1, 2005;269(1-3):112-8.
"Pastes" U.S. Pharmacopeia USP29 downloaded on Sep. 25, 2015 from http://www.pharmacopeia.cn.
Picardo et al. "Acne and rosacea" Dermatology and therapy. Jan. 1, 2017;7(1):S43-S52 (Suppl 1).
Prestidge et al. "Nanoparticle encapsulation of emulsion droplets" International journal of pharmaceutics. Oct. 31, 2006;324(1):92-100.
"Rosacea Causes & Treatment" downloaded Jun. 19, 2018 from: https://www.eruptingmind.com/rosacea-types-causes-treatments/.
Rottman et al. "Sol-Gel Products News: Advanced Sunscreens: UV Absorbers Entrapped in Sol-Gel Glass Microcapsules" Journal of Sol-Gel Science and Technology. Mar. 1, 2002;23(3):268-70.

(56) References Cited

OTHER PUBLICATIONS

Rowe et al. "Handbook of pharmaceutical excipients" Aug. 2009, pp. 155-156, 215-216, 247-249, 311-314; London, Pharmaceutical Press.
Russell et al. "Stable aqueous nanoparticle film assemblies with covalent and charged polymer linking networks" Langmuir. Jul. 3, 2007;23(14):7466-71.
Sacanna et al. "Thermodynamically stable pickering emulsions" Physical review letters. Apr. 12, 2007;98(15):158301.
Saleh et al. "Adsorbed triblock copolymers deliver reactive iron nanoparticles to the oil/water interface" Nano letters. Dec. 14, 2005;5(12):2489-94.
Schueller and Romanowski, eds Conditioning agents for hair and skin. CRC Press, 1999. Table of Contents only (1999).
Shen et al. "A novel process to synthesize magnetic hollow silica microspheres" Colloids and Surfaces A: Physicochemical and Engineering Aspects. Dec. 1, 2007;311(1-3):99-105.
Sheppard SE. "Emulsification at an Oil-Water Interface" The Journal of Physical Chemistry. Dec. 1919;23(9):634-9.
Sheppard SE. "Emulsification by Adsorption at an Oil-Water Interface" J. Phys. Chem 1919 23:634-639.
Shiomi edt al. "Biomimetic Synthesis of Lysozyme—Silica Hybrid Hollow Particles Using Sonochemical Treatment: Influence of pH and Lysozyme Concentration on Morphology" Chemistry of Materials. Sep. 4, 2007;19(18):4486-93.
Simovic et al. "Hydrophilic silica nanoparticles at the PDMS droplet-water interface" Langmuir. Apr. 29, 2003;19(9):3785-92.
Simovic et al. "Adsorption of Hydrophobic Silica Nanoparticles at the PDMS Droplet-Water Interface" Langmuir. Sep. 30, 2003;19(20):8364-70.
Simovic et al. "Nanoparticles of varying hydrophobicity at the emulsion droplet-water interface: adsorption and coalescence stability" Langmuir. Sep. 14, 2004;20(19):8357-65.
Sirard et al. "Steric stabilization of silica colloids in supercritical carbon dioxide" Industrial & engineering chemistry research. Jan. 21, 2004;43(2):525-34.
Škapin et al. "Preparation and coating of finely dispersed drugs: 4. Loratadine and danazol" Journal of Colloid and Interface Science. Apr. 1, 2004;272(1):90-8.
Smooth-On, "Viscosity Scales", undated.
"Sol-Gel", Wikipedia, 2014.
Steinchen A. "From dispersed nano-objects to solutions—A thermodynamic approach" Colloids and Surfaces A: Physicochemical and Engineering Aspects. Jun. 20, 2008;323(1-3):163-6.
Stober process from Wikipedia, http://en.wikipedia.org/wiki/St%C3%B6ber_process, downloaded May 8, 2013.
Strohm et al. "Porous TiO 2 hollow spheres by liquid phase deposition on polystyrene latex-stabilised Pickering emulsions" Journal of Materials Chemistry. 2004;14(17):2667-73.
Sullivan et al. "The effects of inorganic solid particles on water and crude oil emulsion stability" Industrial & Engineering Chemistry Research. Jul. 10, 2002;41(14):3389-404.
Suzuki et al. "Janus microgels prepared by surfactant-free pickering emulsion-based modification and their self-assembly" Journal of the American Chemical Society. Jul. 4, 2007;129(26):8088-9.
"Symptoms and Causes of Vitiligo" Mayo Clinic; obtained online via www.mayoclinic.org on Jun. 4, 2018; pp. 1-3, 2018.
"Symptoms and Causes of Vitiligo" Mayo Clinic; obtained online via www.mayoclinic.org on Jun. 4, 2018; pp. 1-6, 2018.
Sztukowski et al. "Oilfield solids and water-in-oil emulsion stability" Journal of colloid and interface science. May 15, 2005;285(2):821-33.
Takeuchi et al. "Solid dispersion particles of tolbutamide prepared with fine silica particles by the spray-drying method" Powder technology. Mar. 30, 2004;141(3):187-95.
Tarimala et al. "Structure of microparticles in solid-stabilized emulsions" Langmuir. Apr. 27, 2004;20(9):3492-4.
Tatapudy et al. "Benzoyl Peroxide Microcapsules. I. Preparation of core material" Indian drugs. 1995;32(6):239-48.
Technische universitat chemnitz, Catalysis and Surface Science, Lab Course Experiment Pickering Emulsion GC II 6, p. 1-10.
Tissot et al. "Hybrid latex particles coated with silica" Macromolecules. Aug. 14, 2001;34(17):5737-9.
Tjandra et al. "Interaction between silicates and ionic surfactants in dilute solution" Langmuir. Feb. 14, 2006;22(4):1493-9.
"Treating Melanoma Skin Cancer". Obtained online via www.cancer.org on Jun. 4, 2018, pp. 1-7, 2016.
Van Bruggen MP. "Preparation and Properties of Colloidal Core-Shell Rods with Adjustable Aspect Ratios" Langmuir. Apr. 28, 1998;14(9):2245-55.
Van Zuuren et al. "Interventions for rosacea (Review)". Cochrane Database of Systematic Reviews, 2017, 476 pp.
Velikov et al. "Direct observation of the dynamics of latex particles confined inside thinning water-air films" Langmuir. Mar. 3, 1998;14(5):1148-55.
Verginis. "Cutis Benzoyl Peroxide Rosacea Study Summary" downloaded from (http://www.rosacea-treatment-clinic.com.au/Benzoyl-Peroxide/Benzoyl-Peroxide-Acetone.html) (May 2010).
Villalobos et al. "Protective Silica Coatings on Zinc-Sulfide-Based Phosphor Particles" Journal of the American Ceramic Society. Aug. 2002;85(8):2128-30.
"Viscosity" 1-20; www.saylor.org/site/wp-content/uploads/2011/04Niscosity.pdf (.
Voorn et al. "Polymer-clay nanocomposite latex particles by inverse pickering emulsion polymerization stabilized with hydrophobic montmorillonite platelets" Macromolecules. Mar. 21, 2006;39(6):2137-43.
Wang et al. "Effect of Polyelectrolyte Dispersants on the Preparation of Silica-Coated Zinc Oxide Particles in Aqueous Media" Journal of the American Ceramic Society. Aug. 2002;85(8):1937-40.
Wenninger et al., "International Cosmetic Ingredient Dictionary and Handbook" Seventh Edition, vol. 2, pp. 1656-1662 (1997).
Wenninger et al., "International Cosmetic Ingredient Dictionary and Handbook", 2000, aVol. 2, pp. 1140-1147.
Wester et al. "Controlled release of benzoyl peroxide from a porous microsphere polymeric system can reduce topical irritancy" Journal of the American Academy of Dermatology. May 1, 1991;24(5):720-6.
Whitby et al. "Nanoparticle adsorption and stabilisation of surfactant-free emulsions" Journal of colloid and interface science. Sep. 1, 2006;301(1):342-5.
Wiącek et al. "Studies of oil-in-water emulsion stability in the presence of new dicephalic saccharide-derived surfactants" Colloids and Surfaces B: Biointerfaces. Jul. 1, 2002;25(3):243-56.
Wilhelm et al. "On-line tracking of the coating of nanoscaled silica with titania nanoparticles via zeta-potential measurements" Journal of colloid and interface science. Jan. 1, 2006;293(1):88-92.
www.lotioncrafter.com, http://www.lotioncrafter.com/dimethyl-isosorbide-dnti.html downloaded [May 3, 2013].
Xu et al. "Particle bridging between oil and water interfaces" Langmuir. Apr. 24, 2007;23(9):4837-41.
Xu et al. "Preparation of particle-stabilized oil-in-water emulsions with the microchannel emulsification method" Colloids and Surfaces A: Physicochemical and Engineering Aspects. Jul. 15, 2005;262(1-3):94-100.
Yamasaki et al. "Increased serine protease activity and cathelicidin promotes skin inflammation in rosacea" Nature medicine. Aug. 2007;13(8):975.
Yan AC "Current concepts in acne management" Adolescent medicine clinics. Oct. 2006;17(3):613-37.
Yang et al. "Effect of dispersion pH on the formation and stability of Pickering emulsions stabilized by layered double hydroxides particles" Journal of colloid and interface science. Feb. 15, 2007;306(2):285-95.
Yang et al. "Pickering emulsions stabilized solely by layered double hydroxides particles: the effect of salt on emulsion formation and stability" Journal of Colloid and Interface Science. Oct. 1, 2006;302(1):159-69.
Yates et al. "Steric stabilization of colloids by poly (dimethylsiloxane) in carbon dioxide: effect of cosolvents" Journal of colloid and interface science. Jul. 1, 2000;227(1):176-84.

(56) References Cited

OTHER PUBLICATIONS

Yuan et al. "Organic pigment particles coated with colloidal nanosilica particles via layer-by-layer assembly" Chemistry of Materials. Jul. 12, 2005;17(14):3587-94.

Zeng et al. "Particles on droplets: From fundamental physics to novel materials" Solid state communications. Sep. 1, 2006;139(11-12):547-56.

Zhang et al. "Synthesis of silanol-functionalized latex nanoparticles through miniemulsion copolymerization of styrene and γ-methacryloxypropyltrimethoxysilane" Langmuir. May 9, 2006;22(10):4674-9.

Zhou et al. "Clinical characteristics and epidermal barrier function of papulopustular rosacea: A comparison study with acne vulgaris" Pakistan journal of medical sciences. 2016;32(6):1344.

Date, A. A., Naik, B., & Nagarsenker, M. S. (2006). Novel drug delivery systems: potential in improving topical delivery of antiacne agents. Skin Pharmacology and Physiology, 19(1), 2-16.

Fat and why it matters—"The kinds of fats and why it matters to you", Indiana University, Copyright 2019, http://www.indiana.edu/~oso/Fat/Definitions.html.

Büchel, G., Grün, M., Unger, K. K., Matsumoto, A., & Kazuo, T. (1998). Tailored syntheses of nanostructured silicas: control of particle morphology, particle size and pore size. Supramolecular Science, 5(3-4), 253-259.

Huo, Q., Feng, J., Schüth, F., & Stucky, G. D. (1997). Preparation of hard mesoporous silica spheres. Chemistry of Materials, 9(1), 14-17.

Nooney, R. I., Thirunavukkarasu, D., Chen, Y., Josephs, R., & Ostafin, A. E. (2002). Synthesis of nanoscale mesoporous silica spheres with controlled particle size. Chemistry of materials, 14(11), 4721-4728.

Nooney, R. I., Thirunavukkarasu, D., Chen, Y., Josephs, R., & Ostafin, A. E. (2003). Self-assembly of mesoporous nanoscale silica/gold composites. Langmuir, 19(18), 7628-7637.

Ozin, G. A. (1992). Nanochemistry: synthesis in diminishing dimensions. Advanced Materials, 4(10), 612-649.

Zaenglein, A. L., Pathy, A. L., Schlosser, B. J., Alikhan, A., Baldwin, H. E., Berson, D. S., . . . & Keri, J. E. (2016). Guidelines of care for the management of acne vulgaris. Journal of the American Academy of Dermatology, 74(5), 945-973.

Atralin™ (Tretinoin) (2007) Gel prescribing information, FDA, Coria Laboratories Ltd., Jul. 2007, 9 pages.

Kawashima, M. et al. (2014). Is benzoyl peroxide 3% topical gel effective and safe in the treatment of acne vulgaris in Japanese patients? A multicenter, randomized, double-blind, vehicle-controlled, parallel-group study. *The Journal of Dermatology*, 41(9), 795-801.

Patel, V. B. et al. (2001). Clinical assessment of the combination therapy with liposomal gels of tretinoin and benzoyl peroxide in acne. *AAPS PharmSciTech*, 2(3), 1-5.

\* cited by examiner

COMPOSITIONS COMPRISING ENCAPSULATED TRETINOIN

CROSS REFERENCE TO RELATED APPLICATIONS

This application claims the benefit of U.S. Ser. No. 62/531,402, filed on Jul. 12, 2017 which is incorporated in its entirety herein by reference.

FIELD OF THE INVENTION

The present application is directed to compositions comprising encapsulated tretinoin.

BACKGROUND OF THE INVENTION

Topical retinoids are keratinization inhibitors. They work by decreasing the cohesiveness of follicular epithelial cells. This, results in an inhibition in the formation of microcomedones, preventing the formation of mature comedones and inflammatory lesions (Gollnick and Cunliffe, *J. Am. Acad. Dermatol* 2003; 49: S1-38). Use of retinoids promotes the normal desquamation of follicular epithelium. The action of the retinoid may enhance the penetration of other topical compounds used to treat acne.

BPO is a commonly used topical antibacterial agent for acne available either by prescription in combinations or over the counter (OTC). BPO has been found to be lethal to *P. acnes* as well as other bacteria that may reside on the skin. So far there has been no indication of any bacteria developing a resistance to BPO. It has also been demonstrated that BPO has keratolytic activity contributing to its efficacy in treating comedonal acne (Tanghetti, *Cutis*, 2008, 82(5S), 3-11). BPO reduces the cohesiveness of the cells of the stratum corneum, thus improving topical drug delivery through the epidermal barrier.

Silica microcapsule systems have been developed to overcome many of the limitations (such as degradation and irritation) of standard pharmaceutical formulations involving multiple active ingredients. The encapsulation of active ingredients in silica microcapsules serves to protect components in the formulation from interacting with one another and, as a consequence, increases overall formulation stability. Silica is chemically inert, photochemically and physically stable, and safe for topical use.

Clinicians have been reluctant to prescribe topical retinoids and BPO concurrently due to a belief that the BPO may result in oxidation and degradation of the tretinoin molecule, thereby reducing its effectiveness, and prefer to recommend the BPO or an antibiotic/BPO combination to be applied in the morning and tretinoin at night (Yan A C. *Adolesc. Med. Clin.* 2006; 17(3):613-637).

Another publication (Emmy Graber, Treatment of Acne Vulgaris, UpToDate.com, July 2016) states "topical tretinoin should NOT be applied at the same time as benzoyl peroxide", despite the known fact that newer retinoid compositions like Retin A microspheres (MICROSPONGE® System) have less interaction or no short-term interaction with BPO. Obviously, concomitant administration of tretinoin and BPO is taught away by this publication.

BPO is known to oxidize tretinoin and hence it was feared that their interaction on the skin when administered together will diminish the therapeutic effect of tretinoin. Thus, while there are some reports in the literature on the value of both compounds being administered one in the morning and the other in the evening, the verdict up to now was that the two products should not be administered concomitantly.

This belief of the medical profession explains why all previous attempts to solve the stability problem of tretinoin/BPO, such as microencapsulation technology, did not yield a commercial product so far.

Since topical conditions such as acne has multiple pathogenic factors, such as abnormal follicular keratinization, *P. acnes* proliferation and inflammation, combining separate active agents that target these multiple factors would provide the patient with an effective and convenient treatment improving treatment outcomes.

SUMMARY OF THE INVENTION

The inventors of the present invention have found that in order for topical treatment with tretinoin to be effective, especially in combination with BPO, the dissolution rate of the tretinoin component should be reduced to less than 60% wt/h. This is achievable by designing the microcapsules encapsulating solid tretinoin to have a size of less than 50 μm, according to the present invention.

In some embodiments, the present application is directed to an encapsulated tretinoin composition, said composition comprising microcapsules comprising a core comprising tretinoin coated by a shell, wherein said core is in the solid form and said microcapsules have a size of less than about 50 μm.

In other embodiments, the present invention is directed to an encapsulated tretinoin composition, said composition comprising microcapsules comprising a core comprising tretinoin coated by a shell, wherein said core is in the solid form and said microcapsules have a size of less than about 50 μm; and wherein the concentration of all-trans 5,6-epoxy retinoic acid is lower than 1% after two weeks storage at 40° C., in the presence of benzoyl peroxide.

In some embodiments, the present application is directed to an encapsulated tretinoin composition, said composition comprising microcapsules comprising a core comprising tretinoin coated by a shell, wherein said core is in the solid form and said microcapsules have a size of less than about 50 μm, and said composition further comprises encapsulated or non-encapsulated benzoyl peroxide. In another embodiment, the benzoyl peroxide is encapsulated.

In some embodiment, this invention provides an encapsulated tretinoin composition, said composition comprising microcapsules comprising a core comprising tretinoin coated by a shell, wherein said core is in the solid form and said microcapsules have a size of less than about 50 μm; and said composition has tretinoin dissolution rate of less than about 60% weight/h as measured in a medium of 30%:70% V/V mixture of water and isopropyl alcohol at ambient temperature. In other embodiments, the tretinoin dissolution rate is of less than about 40% weight/h.

In other embodiments the composition of this invention comprises microcapsule comprising an encapsulated tretinoin, wherein the microparticle size is between about 5 μm to about 45 μm. In another embodiment between about 30 μm to about 50 μm.

In some embodiments, the compositions of this invention comprise all-trans 5,6-epoxy retinoic acid at a concentration of less than 1%. In other embodiments, at a concentration of less than 0.7%. In some embodiments the degradation of the tretinoin from the composition of this invention is less than 2.5% after two weeks storage at 40° C. In another embodiment, the degradation of said tretinoin is less than 2%.

In some embodiments, the concentration of tretinoin in the composition of this invention is between about 0.01% to about 0.1% weight of the composition. In some embodiments, the concentration of tretinoin in the composition of this invention is between about 0.05% to about 0.1% weight of the composition. In some embodiments, the concentration of tretinoin in the composition of this invention is about 0.075% weight of the composition. In some embodiments, the concentration of benzoyl peroxide in the composition of this invention is about 3% weight of the composition.

In some embodiments, this invention provides a method for treating a surface condition in a subject in need thereof, said method comprising topically administering to said subject a composition of this invention. In other embodiments, the surface is skin or mucosal membrane. In other embodiments, the surface condition is a skin disease, disorder or condition selected from acne, infection, inflammation, pruritus, psoriasis, seborrhea, contact dermatitis, rosacea, and a combination thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF THE PRESENT INVENTION

Thus, in the first aspect, the invention provides a composition comprising tretinoin encapsulated in the core of a microcapsule having a shell, wherein said core is in the solid form and wherein said microcapsule size is less than about 50 μm. In another aspect this invention provides an encapsulated tretinoin composition, said composition comprising microcapsules comprising a core comprising tretinoin coated by a shell, wherein said core is in the solid form and said microcapsules have a size of less than about 50 μm.

As used herein unless otherwise indicated the term "microcapsule" refers to a microparticle having a core shell structure, wherein said core comprises an active agent as defined herein (tretinoin), being coated by a shell forming the microcapsule entrapping the core.

In some embodiments, tretinoin is defined as the core material, i.e. the core of said microcapsule consists of tretinoin alone. In other embodiments, said core of said microcapsule comprises an active agent and at least one Phase Changing Material (PCM), i.e. under these embodiments the core material comprises both the active agent and the PCM. In some embodiments, the coating/shell is directly deposited on the core material. In some embodiments, the coating/shell is directly deposited on the tretinoin forming the core material of said microcapsule. In some embodiments, the core material is solid. In other embodiments, the core material is semi-solid. In some embodiments, the core material consists of a solid particle of the active agent. In other embodiments, the core material comprises a solid particle of the active agent.

In the context of the present invention, the term "core" and/or "core material" used interchangeably herein, refers to the inside/internal part of the microcapsules comprising said active agent, and, in some embodiments also said at least one phase changing material. The core or core material is surrounded by said shell of said microcapsule. It should be noted that additional compounds may be present in said core including for example carriers, excipients, pharmaceutically acceptable polymers or salts etc., all in accordance with the intended use of produced microcapsules, which will be apparent to a skilled artisan preparing said microcapsules.

In some embodiments, the present invention a process for obtaining a thick and dense coating on said core/core material, using in some embodiments metal oxide nanoparticles in combination with a sol-gel precursor, wherein the addition of phase changing material incorporated into said core provides further stability parameters to the encapsulated active agents and to the pharmaceutical composition comprising them.

Thus, in some embodiments of the present invention, there is provided a process for preparing microcapsules having a core encapsulated within a metal oxide shell, said process comprising: (a) preparing an oil-in-water emulsion by emulsification of an oily phase comprising at least one active agent and at least one phase changing material, in an aqueous phase, wherein at least one of said oily phase and aqueous phase comprise a sol-gel precursor; (b) subjecting said emulsion to microcapsule forming conditions; thereby obtaining said microcapsules.

In other embodiments of the invention said core may be solid at room temperature. In other embodiments, said core may be in a semi-solid phase at room temperature. The oily phase utilized by a process of the invention comprises at least one active agent and at least one phase changing material. Said at least one active agent may be in a form of a water insoluble liquid or dispersion in water-insoluble liquid comprising said at least one active agent. The oily phase may be constituted by a liquid water-insoluble active agent; which may comprise a first, liquid water-insoluble active agent dissolved and/or dispersed in a second, water insoluble liquid being another active agent or serving as a carrier. In another embodiment said oily phase may comprise a solid active agent dissolved and/or dispersed in a water-insoluble liquid, being another active ingredient or serving as a carrier. The term "water insoluble liquid" or "dispersion in water-insoluble liquid" refers to a solubility of the liquid (including the ingredients included therein, dissolved and/or dispersed) in water of about less than 1% w/w, preferably 0.5% w/w and most preferably 0.15% w/w at room temperature (20-25° C.). Accordingly, the constituents included in the core whether solid or liquid ingredients have a solubility of about less than 1% w/w, preferably 0.5% w/w and most preferably 0.15% w/w at room temperature (20-25° C.). The water insoluble liquid may be for example squalane polydimethylsiloxane, mineral oil, castor oil, aromatic 200, and mixtures thereof.

In some embodiments the viscosity of said core/core material of said microcapsule (at room temperature) may be about 300 cP, 350 cP, 400 cP, 450 cP, 500 cP, 550 cP, 600 cP, 650 cP, 700 cP, 750 cP, 800 cP, 900 cP, 1000 cP, 2000 cP, 3000 cP, 4000 cP, 5000 cP, 6000 cP, 7000 cP, 8000 cP, 9000 cP, 10,000 cP, 20,000 cP, 30,000 cP, 40,000 cP, 50,000 cP, 60,000 cP, 70,000 cP, 80,000 cP, 90,000 cP, 100,000 cP, 200,000 cP, 300,000 cP, 400,000 cP, 500,000 cP, 600,000 cP, 700,000 cP, 800,000 cP, 900,000 cP or 1,000,000 cP (when measured under various conditions). In some embodiments, the viscosity of said core at room temperature is between about 300 to 600 cP. In other embodiments, the viscosity of said core at room temperature is between about 400 to 500 cP. In further embodiments, the viscosity of said core at room temperature is between about 300 to 10,000 cP. In other embodiments the viscosity of said core at room temperature is between about 5,000 to 1,000,000 cP. In some further embodiments the viscosity of said core at room temperature is between about 20,000 to 1,000,000 cP.

Further input regarding the process of obtaining a core stabilized microcapsule can be found in the International publication WO 2011/080741, which is herein incorporated by reference in its entirety.

In one embodiment, said at least one phase changing material is selected from natural or synthetic paraffins (e.g. having a molecular formula of $C_nH_{n+2}$, wherein n=10–100), $C_{10}$-$C_{100}$ alkane, $C_{10}$-$C_{100}$ alkene (having at least one double bond), $C_{10}$-$C_{100}$ alkyne (having at least one triple bond), aliphatic alcohols (e.g. having a molecular formula of $CH_3(C_2)_nOH$, wherein n=10–100) and fatty acids (e.g. having a molecular formula of $CH_3(CH_2)_{2n}COOH$, wherein n-10–100), or any combination thereof.

In some embodiments, said at least one phase changing material is at least one natural or synthetic paraffin. In some embodiments, said at least one phase changing material is a $C_{10}$-$C_{100}$ aliphatic alcohol (in other embodiments $C_{10}$, $C_{20}$, $C_3$, $C_{40}$, $C_5$, $C_{60}$, $C_{70}$, $C_{80}$, $C_{90}$ to $C_{100}$ aliphatic alcohol). In further embodiments, said at least one phase changing material is a $C_{10}$-$C_{100}$ aliphatic fatty acid (in other embodiments $C_{10}$, $C_{20}$, $C_3$, $C_{40}$, $C_5$, $C_{60}$, $C_{70}$, $C_{80}$, $C_{90}$ to $C_{100}$ aliphatic fatty acid).

In one embodiment said PCMs are liquified (or at least become substantially or partially liquified, pliable or semi-solid, and capable of being handled by a process of the invention) at a temperature range of between about 35° C. to about 60° C., more preferably in a temperature range of between about 35° C. to about 45° C.

Examples of phase changing materials capable of being used by the processes of the invention include, but are not limited to: Carnauba wax (m.p. 82-86° C.), Beeswax pure (m.p. 61-65° C.), Beeswax white pure, (m.p. 61-65° C.), Beeswax bleached technical (m.p. 61-65° C.), Montan wax bleached (m.p. 80-86° C.), Montan wax bleached, partially saponified (m.p. 99-105° C.), Montanic acid (m.p. 81-87° C.), Hydrocarbon wax synthetic (m.p. 106-114° C.), Microcrystalline wax (m.p. 89-95° C.), Microcrystalline wax (m.p. 76-82° C.), Hard ax partially saponified (m.p. 104-109° C.), Beeswax yellow (m.p. 61-66° C.), Polishing Wax (m.p. 78-84° C.), Castor wax (m.p. 83-89° C.), Microwax (m.p. 89-95° C.), Microwax (m.p. 80-86° C.), Microwax (m.p. 76-82° C.), Ozokerite (m. p. 72-79° C.), Microcrystalline wax, plastic (m.p. 76-82° C.), Microcrystalline wax, soft (m.p. 74-80° C.), Wax blend (m.p. 62-68° C.), Polyolefin wax (m.p. 65-75° C.), Lanolin, Shellac, Bayberry wax (m.p. 45° C.), Candelilla wax (m. p. 67-79° C.), Ouricury wax, Rice bran wax (m.p. 77-86° C.), Soy candle (wax), Paraffin (m.p. 47-64° C.), Chinese wax, and any combinations thereof.

In one embodiment of a process for the preparation of a microcapsule, said at least one phase changing material is in a liquid state. Thus, prior to the addition of said at least one PCM, its temperature is raised until it is substantially homogenously liquified. In a further embodiment of the present invention, a process of the invention is carried out under a temperature wherein said at least one phase changing material is in a liquid state, throughout the entire emulsification and encapsulation process disclosed herein above and below. It is noted that said at least one PCM utilized by a process of the present invention, is selected such that its heat of fusion allows for processes of the invention to be carried out substantially without compromising the active agents used, the emulsion formed and the metal oxide shell produced for the microcapsules of the invention.

In one embodiment of a process for the preparation of a microcapsule, at least one metal oxide nanoparticle is added to said aqueous phase prior, during or after emulsification of step (a).

In a further embodiment of a process for the preparation of a microcapsule, the process further comprises a step of cooling obtained microcapsules to room temperature. It is noted that upon cooling of said obtained microcapsules, the viscosity of said core, comprising said at least one active agent and at least one PCM, changes to have values of between about 300 cP to 1,000,000 cP (when measured under various conditions). It should be understood that such PCMB used by a process of the invention are accumulated in the core of obtained microcapsules and are not incorporated in any part of the metal-oxide shell formed by encapsulation process of the invention.

The size of the microcapsules (denoted herein also by the general term "particles" or "microparticles") as will be referred to herein refers to $D_{90}$ meaning that 90% of the particles have the stated dimension or less (measured by volume). Thus, for examples, for spherical particles stated to have a diameter of less than about 50 µm ("microns"), this means that the particles have a $D_{90}$ of 50 microns. The $D_{90}$ (termed also d(0.9)) may be measured by laser diffraction. For particles having a shape other than spheres, the $D_{90}$ refers to the mean average of the diameter of a plurality of particles.

In some embodiments, said microcapsule size is less than about 45 µm. In other embodiments, said microcapsule size is between about 5 µm to about 45 µm. In other embodiments, said microcapsule size is between about 30 µm to about 50 µm. In other embodiments, said microcapsule size is between about 30 µm to about 45 µm. In certain embodiments, the microcapsule size is about 35 µm to about 45 µm.

A composition according to the present invention, wherein the shell of the microcapsules is an inorganic polymeric shell. In some embodiments, the shell is a metal oxide or semi-metal oxide shell. In some embodiments, the metal oxide or semi-metal oxide shell is formed by a sol-gel encapsulation/coating process.

In some embodiments, the metal oxide is selected from silica, titania, alumina, zirconia, ZnO, and mixtures thereof. In some other embodiments, the metal oxide is silica.

According to certain embodiments of the present invention, the surface of the metal oxide layer of the coated particulate matter may be chemically modified by organic groups, in some embodiments hydrophobic groups, attached to its surface. The hydrophobic groups may be for example alkyl groups (such alkyl groups may be further substituted with one or more fluoro atoms), aryl groups (such as benzyl or phenyl), and combinations thereof. The groups may be as described below with respect to the process.

In some embodiments, the microcapsules are formed using a process as disclosed in the following documents (herein incorporated by reference): U.S. Pat. Nos. 6,303,149, 6,238,650, 6,468,509, 6,436.375, US2005037087, US2002064541, and International publication Nos. WO 00/09652, WO00/72806, WO 01/80823, WO 03/03497, WO 03/039510, WO00/71084, WO05/009604, and WO04/81222, disclose sol-gel microcapsules and methods for their preparation; EP 0 934 773 and U.S. Pat. No. 6,337,089 teach microcapsules containing core material and a capsule wall made of organopolysiloxane, and their production; EP0941 761 and U.S. Pat. No. 6,251,313 also teach the preparation of microcapsules having shell walls of organopolysiloxane; U.S. Pat. No. 4,931,362 describes a method of forming microcapsules or micromatrix bodies having an interior water-immiscible liquid phase containing an active, water-immiscible ingredient. Microcapsules prepared by a sol-gel process are also disclosed in GB2416524, U.S. Pat. No. 6,855,335, WO03/066209.

According to some embodiments of the present invention, the coated form of the active ingredient (microcapsule) may be in form of a polymeric microsponge/silica microsphere where the active ingredient is adsorbed, embedded, impregnated or entrapped in the microsponge/silica microshpere as described for example in U.S. Pat. Nos. 4,690,825; 5,145,675, 5,879,716, 5,955,109, and U.S. 9,452,137 incorporated herein by reference in their entirety.

In other embodiments, microcapsules are formed by the encapsulation process disclosed in the following publications (herein incorporated by reference): U.S. Pat. No. 7,629,394, U.S. 9,205,395, US 2015/0328615, US 2014/0186630. Controlled release microcapsules: IN01958CH2007, IN02080CH2007, U.S. Pat. Nos. 4,235,872, 4,670,250, EP 0248531, U.S. Pat. Nos. 4,970,031, 5,238,714, WO9321764, U.S. Pat. No. 5,575,987, WO9420075, US 2004/137031, US 2006/003014, US 2010/180464.

Further according to an embodiment of the present invention the obtained metal oxide coating layer has a width (thickness) of 0.1 μm or above, in some embodiments the metal oxide coating layer has a width (thickness) of 0.1-10 μm.

Additionally, according to an embodiment of the present invention the obtained metal oxide coating layer has a width (thickness) of 0.3 μm or above, in some embodiments the metal oxide coating layer has a width of 0.3-10 μm.

Additionally, according to an embodiment of the present invention, the thickness of the metal oxide layer is in the range of 0.1-10 μm. In some further embodiments, the thickness of the metal oxide layer is in the range of 0.1-3 μm, and in some further embodiments in the range of 0.1-1 μm. The thickness of the metal oxide layer may also be in some embodiments in the range of 0.3 to 3 μm, and in some other embodiments in the range of 0.3 to 2 μm.

Further according to an embodiment of the present invention the obtained metal oxide coating layer has a width (thickness) of about 0.1, 0.2, 0.3, 0.5, 0.7, 1, 1.5, 2 or 5 μm or above, in some embodiments up to 10 μm.

The width of the metal oxide layer may be determined for example by a Transmission Electron Microscope or Confocal Microscope such that in a circular cross sectional area of the particle the smallest width is at least e.g. 0.1 μm (the width is determined as the smallest distance from the surface of the particle (i.e. metal oxide surface) to the core-metal oxide interface).

The microcapsules are in some embodiments characterized in that the core material is substantially free of the metal oxide and further in that the metal oxide layer is substantially free of the core material, e.g. either as particle dispersion (in the nano-metric range of below 0.1 μm) of the particulate matter or as molecular dispersion of the particulate matter.

Thus, according to an embodiment of the present invention, the metal oxide layer is substantially free of core material (either in the form of molecules or as nano-metric particles). The term "substantially free" in this context denotes that the concentration of the molecules of the core material or the concentration of the nano-metric particles of the core material is negligible as compared to the metal oxide. Similarly, by the term "the core material is substantially free of the metal oxide" is meant that the concentration of the metal oxide in the core is negligible as compared to the core material.

According to another embodiment when the microcapsules are prepared by a method such as spray drying, the core material comprising the active agent may further comprise up to about 30% w/w, in some embodiments up to about 20% metal oxide and the metal oxide coating layer may further comprise up to about 30% w/w, in some embodiments up to about 20% w/w of the active agent.

According to an embodiment of the present invention the weight ratio of the metal oxide to the solid particulate matter is in the range of 1:99 to 50:50. The weight ratio of the metal oxide layer to the solid particulate matter may be also in the range of 3:97 to 50:50, 5:95 to 50:50, 10:90 to 50:50, 5:95 to 30:70, 10:90 to 30:70. Further, according to an embodiment of the present invention the rate ratio of the metal oxide to the solid particulate matter is in the range of 10:90 to 20:80.

According to another embodiment of the present invention, when spray drying method is used, the weight ratio of the metal oxide to the solid particulate matter may be in the range 5:95 to 95:5.

In some embodiments, said composition of the invention has tretinoin dissolution rate of less than about 60% weightth as measured in a medium of 30%:70% V/V mixture of water and isopropyl alcohol at ambient temperature. In some further embodiments, said tretinoin dissolution rate is less than about 40% weight/h.

It should be noted that the dissolution rate (release rate) defined herein relates to the measurement (either in vitro or in vivo) of the rate at with the active agents tretinoin) is released from the topical medicament of the invention, to the extracting media or skin. The release rate is measured using known method as defined herein, i.e. 70% IPA (isopropyl alcohol) and 30% water and optionally an antioxidant (such as BHT) at room temperature.

In some embodiments, a composition of the invention further comprises benzoyl peroxide (BPO), as a second active agent.

In some embodiments, said BPO is non-encapsulated in a composition of the invention. In another embodiments, said BPO is encapsulated in a separate microcapsule (i.e. "BPO microcapsule", a microcapsule that is different and separated from the microcapsule encapsulating the tretinoin ("tretinoin microcapsule") in a composition of the invention). In some embodiments, said microcapsule encapsulating said BPO has a shell different than the shell of said tretinoin microcapsule. In other embodiments, said microcapsule encapsulating said BPO has a shell similar to the shell of said tretinoin microcapsule (i.e. it is formed using similar encapsulating processes or similar encapsulating reagents). In some embodiments, the shell of said BPO microcapsule is a metal oxide shell. In some embodiments, said BPO is in the solid form. In other embodiments, said BPO microcapsule has a solid core. In other embodiments, said BPO microcapsule consists of solid BPO. In other embodiments, said shell of said BPO microcapsule is directly deposited on solid BPO.

As used herein by the term "non-encapsulated form" or "non-coated form" is meant that the active ingredient (BPO) is present in the composition in its "naked" form meaning that it is not intimately embedded, encapsulated, entrapped or encased in a polymeric carrier, and is present in the composition in direct contact with the composition carrier. As used herein by the term "coated form of the active ingredient" is meant that the active ingredient is embedded, dispersed, entrapped, or encased, e.g. as a solid dispersion or molecular dispersion in a polymeric carrier which may be an organic or inorganic carrier and which may serve as a matrix for dispersing the active ingredient or as encapsulated material coating said active ingredient (i.e the active ingredient is present in a core or is a core material encapsulated by a shell composed of a polymeric material which may be an organic or inorganic polymer).

In some embodiments wherein said composition of the invention further comprises BPO, the concentration of RRT (relative retention time) 0.44 (all-trans 5,6-epoxy retinoic acid) is lower than 1% after two weeks storage at 40° C. In other embodiments, the concentration of RRT 0.44 (all-trans 5,6-epoxy retinoic acid) is lower than 0.7% after two weeks storage at 40° C.

Figure 1:
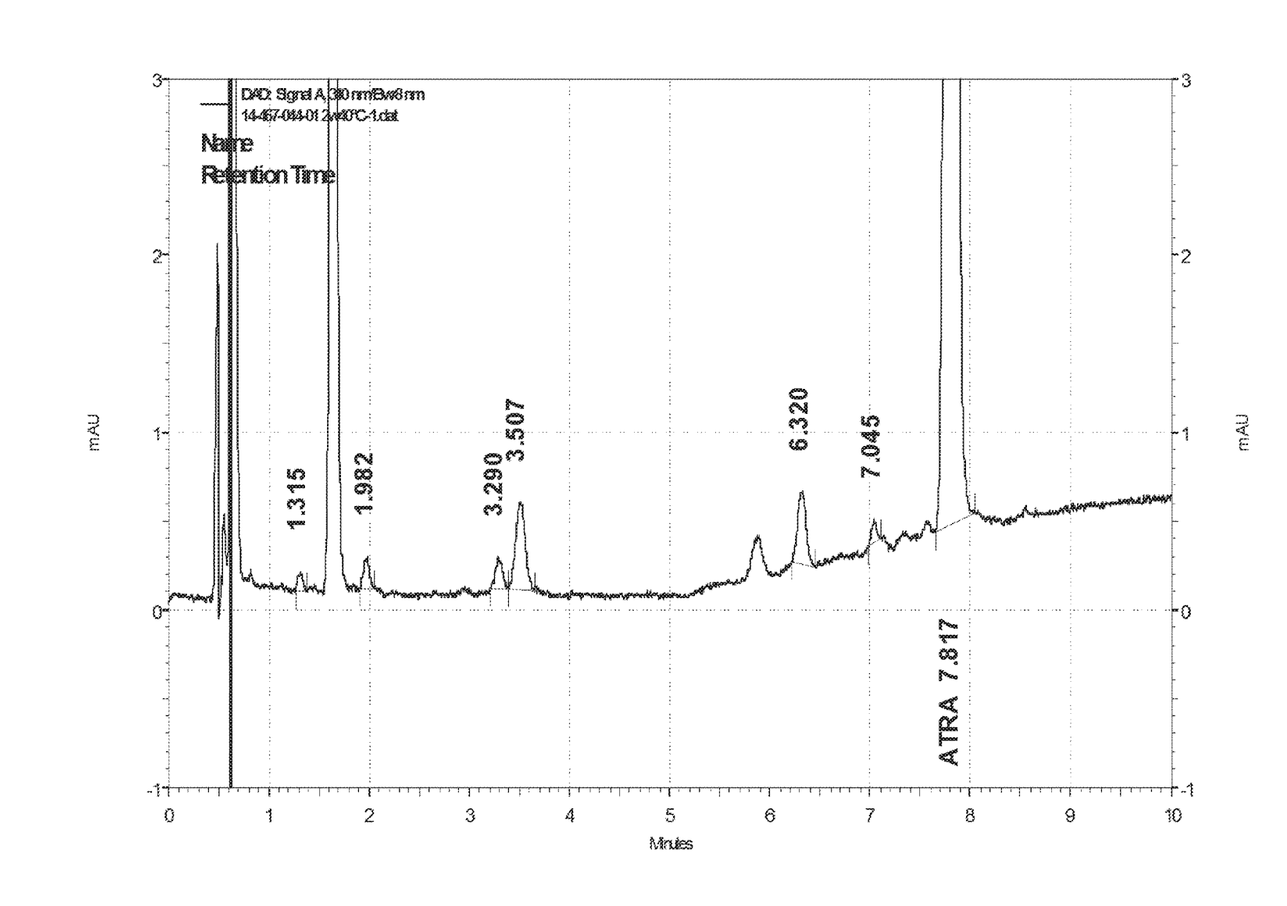
FIG. 1 shows the HPLC chromatogram of an embodiment composition of the invention comprising 0.05% E-ATRA and 3% E-BPO eluted with acetonitrile and acetic acid 1% in water on a Zorbax RX-C18 3.5 mμ, 4.6*75 mm column, showing the RRT 0.44 product (all-trans 5,6-epoxy retinoic acid at retention time of about 3.5 min (RRT product calculated relative to the ATRA peak at 7.8 min).

When referring to RRT 0.44 it should be understood to relate to the degradation product of tretinoin in the presence of BPO as shown in the HPLC chromatography of the composition of the invention after two weeks of storage at 40° C. An example of the RRT product can be seen in FIG. 1 at retention time 3.507 min. In other embodiments, RRT 0.44 refers to all-trans 5,6-epoxy retinoic acid (CAS 13100-69-1) represented by the following structure:

In some embodiments wherein said composition of the invention further comprises BPO, the degradation of said tretinoin is less than 2.5% after two weeks storage at 40° C. In other embodiments, the degradation of said tretinoin is less than 2%.

In some embodiments, wherein the composition of the invention further comprises BPO, the degradation of said tretinoin is not more than 5% after 18 or 24 months storage at 2° C.-8° C. In other embodiments, the degradation of said tretinoin is not more than 5% after 3 months storage at 25° C. and 60% RH.

In some embodiments, said medicament is administered in a single composition, single fixed dose medicament, comprising both said active agents (BPO and tretinoin). The term "fixed dose medicament" should be understood as meaning a combination whose active agents are combined at fixed doses in the same vehicle (single formula) that delivers them together to the point of application.

In further embodiments, said medicament comprises two separate compositions each one comprising each of said active agents. In such embodiments the weight % amount of each active agent relates to each of their weight amount in each composition separately. In some embodiments, said two separate compositions of said medicament are administered concomitantly. In further embodiments, said two separate compositions are administered sequentially.

In some embodiments, a composition of the invention comprises tretinoin is in the amount of between about 0.01% to about 0.1% weight of the composition.

In some embodiments, a composition of the invention comprises tretinoin is in the amount of between about 0.05% to about 0.1% weight of the composition.

In some embodiments, a composition of the invention comprises tretinoin is in the amount of about 0.075% weight of the composition.

In other embodiments, a composition of the invention comprises BPO is an amount of about 3% weight of the composition.

In another embodiment, a composition of the invention comprises tretinoin in an amount of about 0.1% weight and benzoyl peroxide in an amount of about 3% weight. In another embodiment, a composition of the invention comprises tretinoin in an amount of about 0.05% weight and benzoyl peroxide in an amount of about 3% weight.

In one embodiment, the term "about", refers to a deviance of between 0.0001-5% from the indicated number or range of numbers. In one embodiment, the term "about", refers to a deviance of between 1-10% from the indicated number or range of numbers.

In some embodiments, the composition of this invention is a pharmaceutical composition. The term "pharmaceutical composition" means a composition suitable for pharmaceutical use as defined herein. In another embodiment, the pharmaceutical composition comprises a suitable carrier or diluent. The pharmaceutical composition of this invention includes a therapeutically effective amount of the active ingredient, i.e. the amount which provides a therapeutic effect for a given condition and administration regimen.

The active component can be formulated into the composition as its hydrate, solvate, or as its pharmaceutically acceptable salt. Suitable pharmaceutically acceptable salts of the active component(s) (i.e. tretinoin) of this invention include inorganic salts such as: ammonium, alkali metals to include lithium, sodium, potassium, cesium; alkaline earth metals to include calcium, magnesium, aluminium; zinc, barium; or quaternary ammoniums; or organic salts such as arginine, organic amines to include aliphatic organic amines, aromatic amines, t-butylamines, (N-benzylphenethylamine), dicyclohexylamines, dimethylamines, diethanolamines, ethanolamines, ethylenediamines, imidazoles, lysines, methylamines, N-methyl-D-glucamines, N,N'-dibenzylethylenediamines, pyridines, picolinates, piperazines, tris(hydroxymethyl)methylamines, triethylamines, triethanolamines, trimethylamines, or ureas.

In some embodiment, a composition of the invention is a topical medicament. The term "topical medicament" as used herein should be understood to encompass any pharmaceutical formulation that enables the administration of the active agents to a skin tissue of a patient administered with said medicament. The composition or topical medicament of the present invention comprises a carrier. According to an embodiment of the present invention the carrier is in the form of an ointment, a cream, a lotion, an oil, a solution (in some embodiments an aqueous solution), an emulsion, a gel, a paste, a milk, an aerosol, a powder, or a foam, each represents another embodiment of this invention. In some embodiments, the carrier is an aqueous-based carrier (such as a gel, oil-in water emulsion or oil-in water cream, aqueous solution, foam, lotion, spray).

In yet another aspect, the present invention provides a method for treating a surface condition (e.g., a skin disease or disorder) in a subject in need thereof, comprising topically administering to the subject an effective amount of a composition as described herein. In certain embodiments, the surface is skin or mucosal membrane. In some embodiments, the surface condition is a skin disease, disorder or condition selected from acne, infection, inflammation, pruritus, psoriasis, seborrhea, contact dermatitis, rosacea, melasma, photoaging, photodamage, fine wrinkles, and a combination thereof, each represents another embodiment of this invention. In another embodiment, the method of this invention is directed for treating acne.

The term "treating" or "treatment" as used herein includes any treatment of a condition, disease or disorder associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical drugs and biologicals, Rahway, N.J.; Merck & Co; 1989., incorporated herein by reference in its entirety.

Although individual needs may vary, determination of optimal ranges for effective amounts of the compositions is within the skill of the art. Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

Thus, the final form of the composition may be any of the above forms, mentioned with respect to the carrier, where the microcapsules are dispersed in the carrier. The final form of the composition may also be in the form of a wash or cleanser.

The following examples are presented in order to more fully illustrate the preferred embodiments of the invention. They should in no way, however, be construed as limiting the broad scope of the invention.

EXAMPLES

Example 1

Preparation of Formulation of Encapsulated KIRA (0.05%) and Encapsulated BPO (3%)
Oil Phase:
  2000.0 grams of Cyclomethicone 5N, 1500.0 grams of Cetyl Alcohol, and 1500.0 grams of Mono- and di-Glycerides were mixed and heated to 70° C. until melting. 200.0 grams of Carbopol 980 NF were added and the oily phase was mixed and heated until addition to the main reactor.
Water Phase:
  Weight in SOL Reactor (main reactor)
  50.0 grams of Ethylenediaminetetraacetate Disodium salt, 1000.0 grams of Macrogol Stearate Type I, 2000.0 grams of Glycerin (99.5%) and 125.0 grams of Imidurea were dissolved into 29.0 kilograms of water. The solution was mixed and heated to 65° C. until addition of the oily phase to the main reactor.
E-BPO/Citric Acid Phase:
  100.0 grams of Anhydrous Citric Acid were added into 10,000.0 grams of 15% encapsulated benzoyl peroxide water suspension. The suspension was mixed and heated to 45-50° C. until addition to the main reactor.
Emulsion: Main Reactor
  The oily phase was added to the water phase under circulation and mixing at 65° C. for 5 minutes. The resulting emulsion was homogenized, mixed and circulated under vacuum for 20 minutes then additional 10 minutes after adding 200.0 grams of NaOH 20% solution. E-BPO/Citric acid phase was added to the emulsion under moderate mixing and circulation then mixing was continued for 15 minutes. The emulsion pH was adjusted to 4 by HCl 10% solution titration. 694.4 grams of encapsulated ATRA 3.6% water suspension were added to 55° C. emulsion during mixing then water was added until the total weight of the emulsion reached 50 kilograms and mixed for 5 minutes. The emulsion continued mixing for 90 minutes during cool down to 30° C.

Example 2

Table I below shows the particle size distribution of eight E-ATRA suspensions (the left side of the Table) and its influence on the stability of the cream formulations (the right side of the table). The eight cream formulations were prepared from the eight E-ATRA suspensions. The differences between the various suspensions is the manufacturer of the critical raw materials. As can be seen from the table the particle size distribution of the suspensions influences the percentage of the ATRA degradant RRT 0.44 (all-trans 5,6-epoxy retinoic acid) and the % degradation of ATRA in the cream formulations after stability of 2 weeks at 40° C./75% RH.

TABLE 1

Influence of particle size distribution (PSD) on stability of the corresponding cream

| E-ATRA 3.6% suspension | | | E-ATRA, 0.05% & E-BPO, 3% cream | | | | |
|---|---|---|---|---|---|---|---|
| | PSD, µm | | | TZ | 2 w 40° C. | | |
| | | | | | | all-trans | |
| Batch # | d(0.1) | d(0.9) | Batch # | ATRA assay | ATRA assay | 5,6-epoxy retinoic acid | % degradation |
| 450-140-01 | 5 | 49 | 458-014-01 | 0.0506 | 0.0494 | 0.74 | 2.37 |
| 458-007-01 | 12 | 42 | 458-034-01 | 0.0508 | 0.0501 | 0.57 | 1.38 |
| 458-010-01 | 4 | 54 | 458-031-01 | 0.0507 | 0.0492 | 1.14 | 2.96 |
| 458-037-01 | 6 | 41 | 458-043-01 | 0.0515 | 0.0513 | 0.54 | 0.39 |
| 467-089-01 | 13 | 40 | 467-101-01 | 0.0513 | 0.0510 | 0.31 | 0.58 |
| 467-111-01 | 5 | 34 | 467-118-01 | 0.0512 | 0.0514 | 0.24 | 0.00 |

TABLE 1-continued

Influence of particle size distribution (PSD) on stability of the corresponding cream E-ATRA, 0.05% & E-BPO, 3% cream

| E-ATRA 3.6% suspension | | | TZ | 2 w 40° C. | | |
|---|---|---|---|---|---|---|
| PSD, μm | | | | | all-trans | |
| Batch # | d(0.1) | d(0.9) | Batch # | ATRA assay | ATRA assay | 5,6-epoxy retinoic acid | % degradation |
| 467-007-01 | 15 | 41 | 401-146-01 | 0.0508 | 0.0500 | 0.42 | 1.57 |
| 401-138-01 | 5 | 44 | 467-023-01 | 0.0559 | 0.0548 | 0.43 | 1.97 |

PSD—particle size distribution,
TZ—time-zero,
2 w 40° C.—2 weeks at 40° C.

TABLE 2

Stability data of E-ATRA, 0.05% & E-BPO, 3% cream after 3, 18 or 24 months storage

| | ATRA Assay | | | |
|---|---|---|---|---|
| Batch# | Time zero | 3 m at 25° C. | 18 m at 2° C.-8° C. | 24 m at 2° C.-8° C. |
| P3156-00315 | 0.0494 (98.8%) | 0.0491 (98.2%) | 0.0489 (97.8%) | 0.0486 (97.2%) |
| P3156-00116 | 0.0504 (100.8%) | 0.0479 (95.8%) | 0.0479 (95.8%) | 0.0478 (95.6%) |

TABLE 3

Stability data of E-ATRA, 0.1% & E-BPO, 3% cream after 3, 18 or 24 months storage

| | ATRA Assay | | | |
|---|---|---|---|---|
| Batch# | Time zero | 3 m at 25° C. | 18 m at 2° C.-8° C. | 24 m at 2° C.-8° C. |
| P3149-00115 | 0.0973 (97.3%) | 0.0962 (96.2%) | 0.0955 (95.5%) | 0.0943 (94.3%) |
| P3149-00116 | 0.099 (97.7%) | 0.0949 (94.9%) | 0.0971 (97.1%) | 0.0954 (95.4%) |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A composition comprising:
   microcapsules comprising tretinoin, wherein:
      said microcapsules comprise a core containing tretinoin dispersed in an oil and a phase changing material and a metal oxide shell; and
      wherein said tretinoin is in solid form and said microcapsules have a $D_{90}$ between 30 μm to 50 μm; and
      wherein said tretinoin is in the range of 0.01%-0.1% by weight of the composition; and
   microcapsules comprising solid benzoyl peroxide with a metal oxide shell; wherein said benzoyl peroxide is in an amount of 3% by weight of the composition;
   wherein degradation of said tretinoin is less than 2.5% after two weeks storage at 40° C. and 75% relative humidity.

2. The composition according to claim 1, wherein said tretinoin is in the amount of between 0.05% and 0.1% weight of the composition.

3. The composition according to claim 2, wherein said tretinoin is in the amount of 0.075% weight of the composition.

4. The composition according to claim 1, wherein the composition comprises a carrier, wherein the carrier is in the form of an ointment, a cream, a lotion, an oil, a solution, an emulsion, a gel, a paste, a milk, an aerosol, a powder, or a foam.

5. The composition according to claim 1, wherein the concentration of all-trans 5,6-epoxy retinoic acid after two weeks storage at 40° C. and 75% relative humidity is less than 1% by weight of the initial tretinoin amount prior to storage.

6. The composition according to claim 1, wherein the degradation of said tretinoin is less than 2%.

7. The composition according to claim 1, wherein the degradation of said tretinoin is not more than 5% by weight of the initial tretinoin amount, after 18 or 24 months storage at 2° C.-8° C.

8. The composition according to claim 1, wherein the degradation of said tretinoin is not more than 5% by weight of the initial tretinoin amount, after 3 months storage at 25° C. and 60% RH.

9. The composition according to claim 1, wherein the composition comprises a carrier, wherein the carrier is in the form of an ointment, a cream, a lotion, an oil, an emulsion, or a gel.

10. The composition according to claim 9, wherein the amount of said tretinoin is 0.1% weight of the composition and the amount of said benzoyl peroxide is 3% weight of the composition.

11. The composition of claim 1, wherein said composition has a tretinoin dissolution rate of less than 60% weight/h as measured in a medium of 30%:70% V/V mixture of water and isopropyl alcohol at ambient temperature.

12. The composition according to claim 11, wherein said composition has a tretinoin dissolution rate of less than 40% weight/h.

13. A method for treating a skin disease, disorder or condition selected from acne, infection, inflammation, pruritus, psoriasis, seborrhea, contact dermatitis, rosacea, melasma, photoaging, photodamage, fine wrinkles, and a combination thereof in a subject in need thereof, said method comprising topically administering to said subject a composition according to claim 1.

14. A method for treating a skin disease, disorder or condition selected from acne, infection, inflammation, pruritus, psoriasis, seborrhea, contact dermatitis, rosacea, melasma, photoaging, photodamage, fine wrinkles, and a combination thereof in a subject in need thereof, said method comprising topically administering to said subject a composition according to claim 11.

\* \* \* \* \*